US00PP28379P3

(12) United States Plant Patent
Suphachadiwong

(10) Patent No.: US PP28,379 P3
(45) Date of Patent: Sep. 12, 2017

(54) ***VANDA* PLANT NAMED 'SPCDW1504'**

(50) Latin Name: ***Vanda* Jones ex R. Br.**
Varietal Denomination: SPCDW1504

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 65 days.

(21) Appl. No.: 14/998,797

(22) Filed: Feb. 17, 2016

(65) Prior Publication Data

US 2016/0249513 P1 Aug. 25, 2016

(30) Foreign Application Priority Data

Feb. 20, 2015 (QZ) ..... PBR 2015/0404

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Vanda* cultivar named 'SPCDW1504' which is characterized by sepals and petals with a unique purple color, sepals and petals which are heavily dotted and blotched red-purple and purple, and the stability of these characteristics from generation to generation.

4 Drawing Sheets

Latin name of the genus and species: The Latin name of the genus and species of the novel variety disclosed herein is *Vanda* Jones ex R. Br.

Variety denomination: The inventive variety of *Vanda* spp. disclosed herein has been given the variety denomination 'SPCDW1504'.

CROSS REFERENCE TO RELATED APPLICATIONS

This application claims priority to the Community Plant Variety Rights application number 2015/0404, filed Feb. 20, 2015, which is herein incorporated by reference.

BACKGROUND OF THE INVENTION

Parentage: The *Vanda* variety 'SPCDW1504' originated as a naturally occurring, whole-plant mutation of *Vanda* 'SPCDW0801' (unpatented in the United States, Community Plant Variety Rights grant number 28272), a variety developed and owned by the inventor. The inventor of 'SPCDW1504' is a commercial producer of *Vanda* and regularly discovers mutations at his greenhouse operation in Bangphra, Thailand. The variety now called 'SPCDW1504' was initially discovered in November of 2008 as one such mutation of 'SPCDW0801'.

Asexual Reproduction: Asexual reproduction of the new cultivar 'SPCDW1504', by way of mericloning, was first initiated in November of 2008 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1504' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1504'. These characteristics in combination distinguish 'SPCDW1504' as a new and distinct *Vanda* cultivar:

1. *Vanda* 'SPCDW1504' exhibits sepals and petals with a unique purple color; and
2. *Vanda* 'SPCDW1504' exhibits sepals and petals which are heavily dotted and blotched red-purple and purple.

BOTANICAL DESCRIPTION OF THE PLANT

Figure 1:
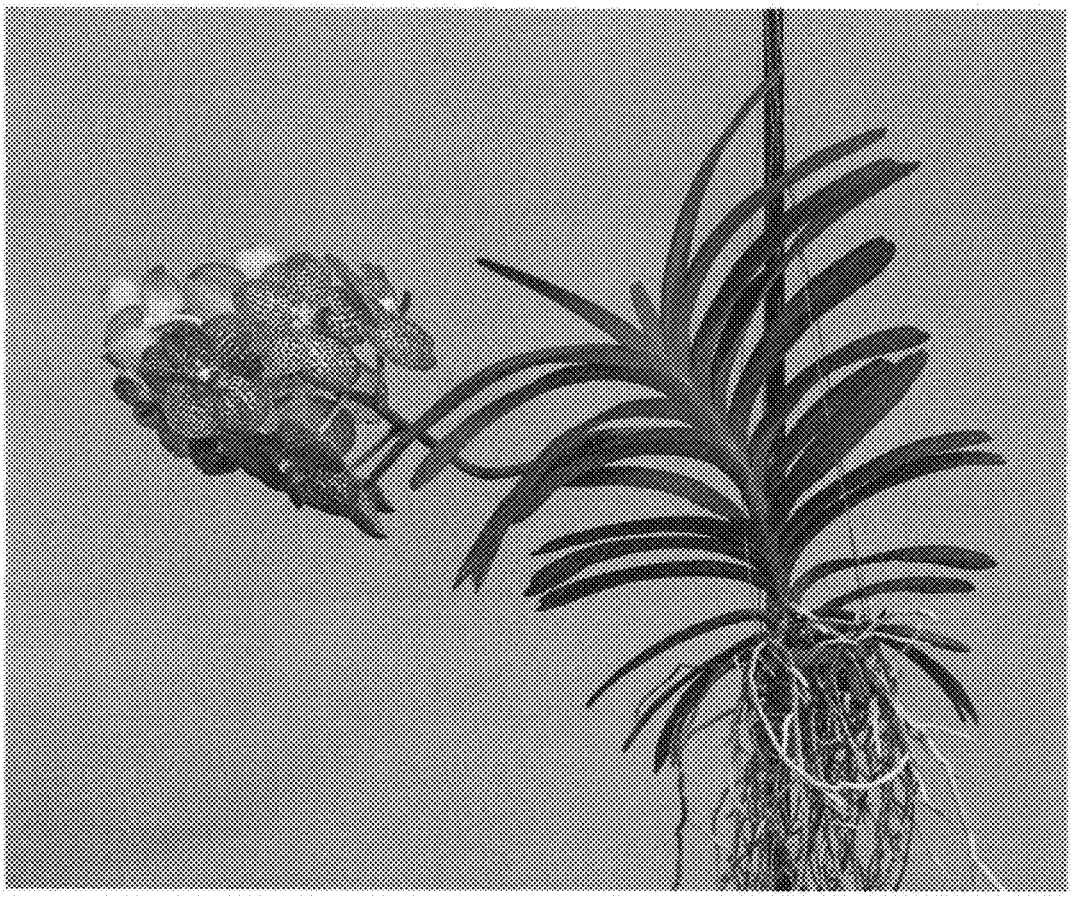
FIG. 1 illustrates, as nearly true as it is reasonably possible to make the same in color photographs of this type, an exemplary plant of 'SPCDW1504' grown in a commercial greenhouse in Honselersdijk, the Netherlands. This plant is approximately 6 years old from the time of mericloning, shown planted in an 8 by 8 cm container.
Figure 2:
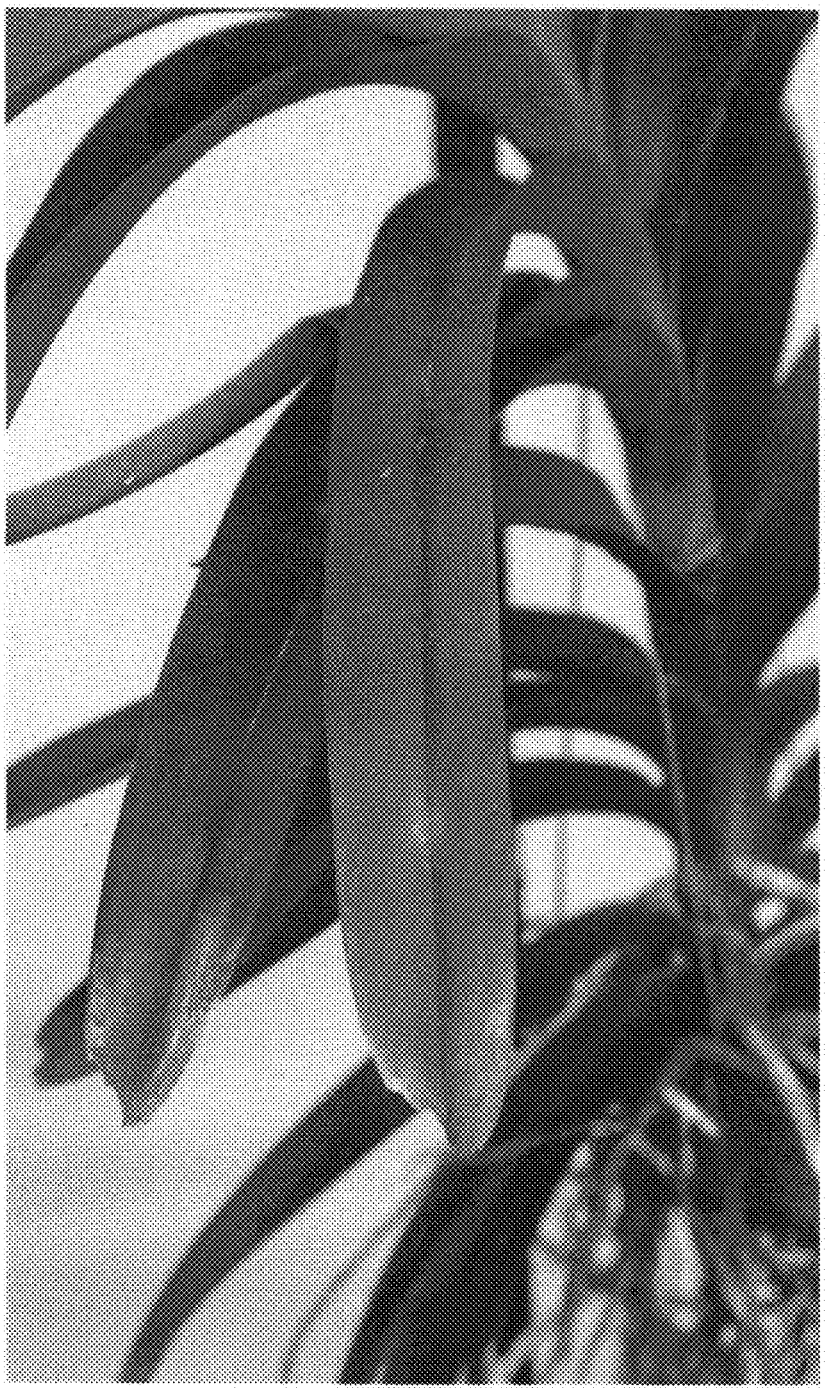
FIG. 2 illustrates, as nearly true as it is reasonably possible to make the same in color photographs of this type, the typical foliage of 'SPCDW1504'.
Figure 3:
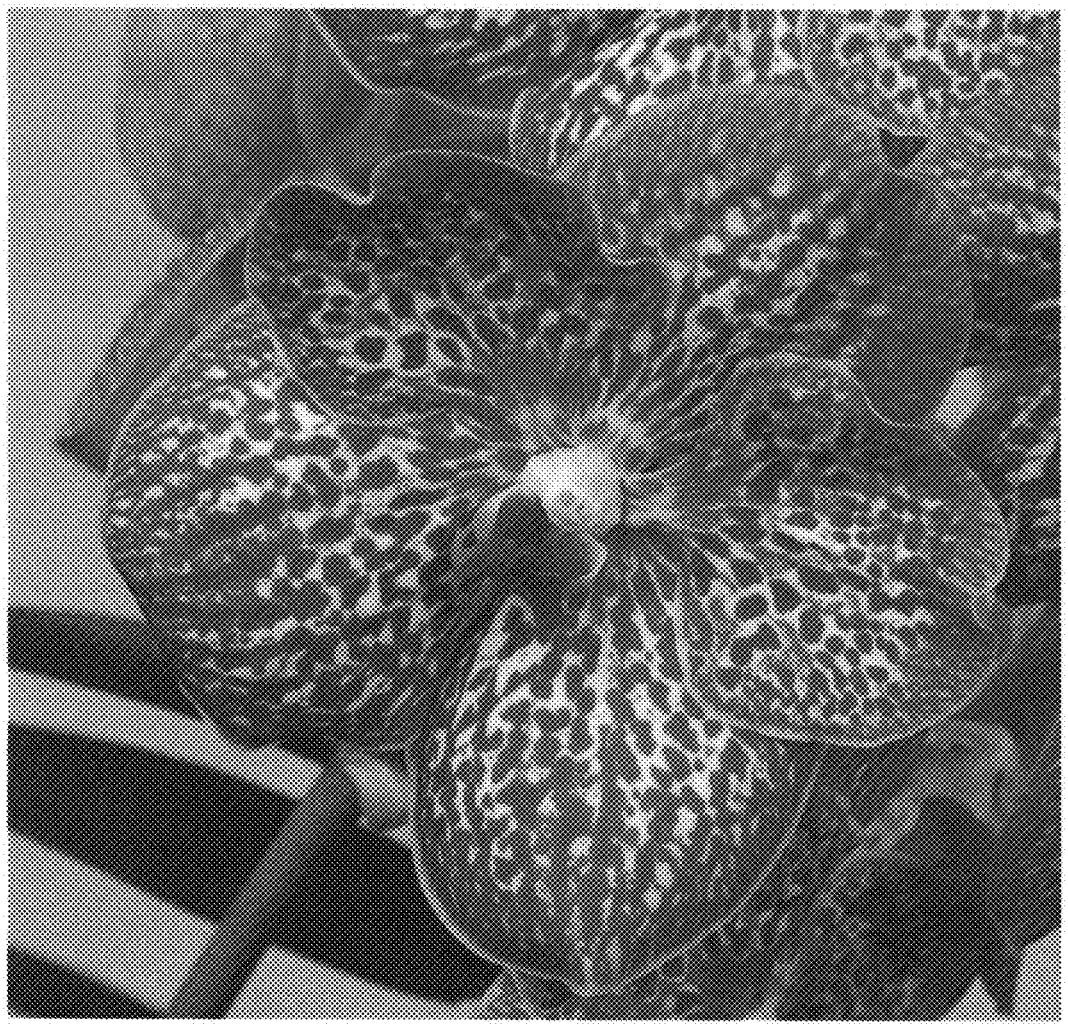
FIG. 3 illustrates, as nearly true as it is reasonably possible to make the same in color photographs of this type, the typical flower of 'SPCDW1504'.
Figure 4:
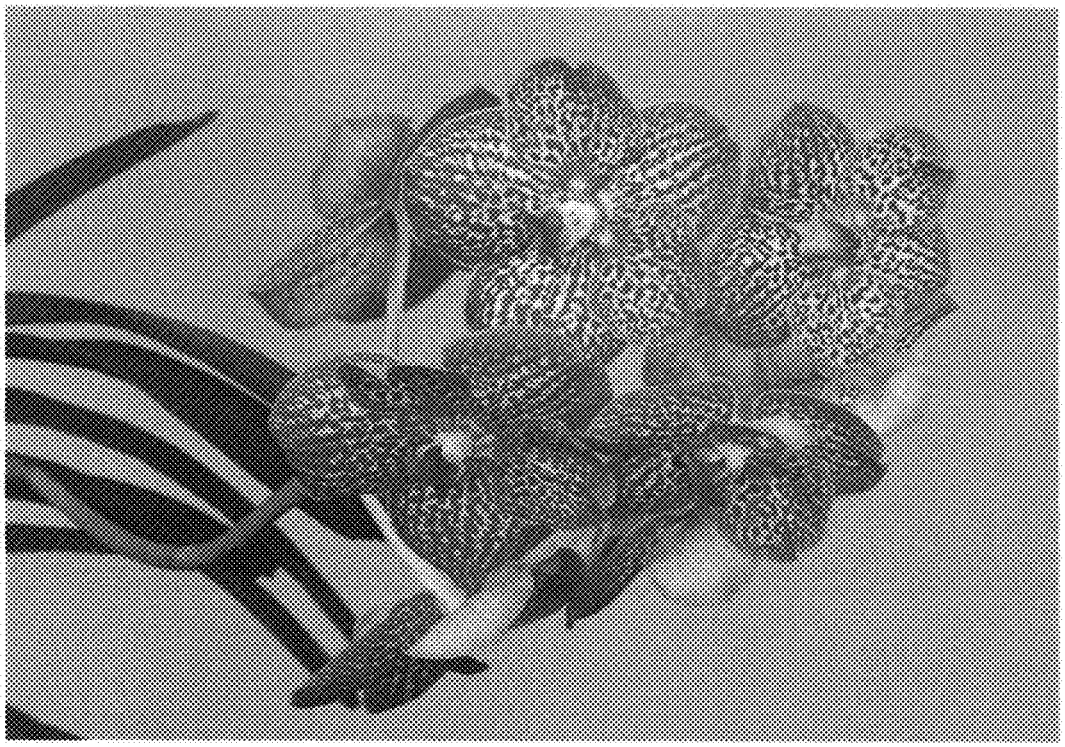
FIG. 4 illustrates, as nearly true as it is reasonably possible to make the same in color photographs of this type, the typical inflorescence of 'SPCDW1504'.

The following observations and measurements made in January of 2016 describe averages from a sample set of six specimens of six year-old 'SPCDW1504' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1504' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1504' and comparisons with other varieties of *Vanda* are provided below.

Plant description:

- *Growth habit*.—Perennial; monopodial, upright. Single monopodial leafy stem, with flowers carried slightly above the leaf plane, inflorescences grow from the leaf axils.
- *Average height from base (plant grown in hanging basket, so no soil line present) to foliar plane*.—42.4 cm.
- *Average height from base (plant grown in hanging basket, so no soil line present) to top of floral plane*.—47.5 cm.
- *Plant spread*.—Average of 54.2 cm.
- *Appropriate container size*.—8 cm by 8 cm rectangular hanging basket.
- *Growth rate*.—Moderate.
- *Plant vigor*.—Moderate.
- *Propagation type*.—Tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility*.—Similar to other *Vanda* varieties.
- *Environmental tolerances*.—Adapt to, at least, USDA Zones 11 and 12 and temperatures as high as 40 degrees Celsius; high tolerance to rain; moderate to high tolerance to wind.

Root system:

- *General*.—Densely rooting; with aerial roots only.
- *Dimensions, mature roots*.—62.0 cm long with a diameter of 0.5 cm, on average.
- *Texture*.—Very fleshy; non-fibrous.
- *Color*.—Greyed-Green, near RHS 192C to 192D; root apex is yellow-green, RHS 146A.

Stem:

- *Branching habit*.—Monopodial; no lateral branches present.
- *Number of primary (main) stems per plant*.—One.
- *Number or secondary (lateral) branches per plant*.—None.
- *Appearance and shape*.—Circular, formed by the leaf sheaths.
- *Length*.—23.0 cm.
- *Diameter*.—1.1 cm.
- *Internode length*.—0.3 cm.
- *Luster*.—Matte.
- *Aspect*.—Near vertical.
- *Strength*.—Very strong.
- *Color, juvenile*.—Yellow-green, near RHS 145C.
- *Color, mature*.—Yellow-green, near RHS 145C.
- *Color at internodes*.—Yellow-green, near RHS 145C.
- *Pubescence*.—Glabrous.

Foliage:

- *Arrangement*.—Distichous.
- *Quantity*.—Approximately 25 leaves per plant.
- *Dimensions*.—25.4 cm long and 3.1 cm wide, on average.
- *Shape of blade*.—Ligulate; moderately carinate.
- *Aspect*.—Moderately curved.
- *Apex*.—Unequal praemorse.
- *Base*.—Sheathing.
- *Sheath dimensions*.—3.8 cm long and 1.5 cm wide, on average.
- *Sheath color*.—Yellow-green, in between RHS 145B.
- *Margin*.—Entire.
- *Pubescence, texture and luster of adaxial surface*.—Glabrous, smooth, and very slightly glossy.
- *Pubescence, texture and luster of abaxial surface*.—Glabrous, smooth, and matte.
- *Color*.—Juvenile foliage, adaxial surface — Green, near RHS 143B, and darker towards the margins, near RHS 137B. Juvenile foliage, abaxial surface — Green, near RHS 143A. Mature foliage, adaxial surface — Green, near RHS NN137A. Mature foliage, abaxial surface — Yellow-green RHS 146B.
- *Venation*.—Parallel.
- *Venation color, adaxial surface*.—Green, near RHS NN137A.
- *Venation color, abaxial surface*.—Yellow-green RHS 146A.
- *Petiole*.—No petioles present, leaves sessile.

Inflorescence:

- *Inflorescence arrangement*.—Axially placed raceme.
- *Natural flowering season*.—Autumn into winter.
- *Time to flower*.—Approximately 10 months.
- *Flowers per inflorescence*.—Average of 11; 10 open flowers and 1 bud.
- *Inflorescence height*.—Approximately 27.5 cm (measured from base of lowest flower to top of upper flower).
- *Inflorescence diameter*.—Approximately 19.1 cm.
- *Peduncle*.—Dimensions — Approximately 38.7 cm long and 0.8 cm wide. Aspect — Generally at a 50 degree angle to lateral branch axis. Strength — Moderately strong. Texture and luster — Glabrous and moderately glossy. Color — Green, RHS 143A.

Bud:

*Length*.—Average of 1.6 cm.

*Diameter*.—Average horizontal diameter is 1.8 cm; the vertical diameter is 2.3 mm.

*Shape*.—Cubic, with a deltoid apex which is pointed downward.

*Pubescence, texture and luster*.—Glabrous, smooth and moderately glossy.

*Color*.—Greyed-purple, near RHS 183D; apex is darker, near RHS 138B; based is tinged yellow-green, near 149B to 149C. Buds are moderately dotted red-purple near RHS 71A.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum.

*Aspect*.—Flowers are outward-facing to slightly nodding.

*Vertical height*.—Approximately 11.3 cm.

*Diameter*.—Approximately 10.5 cm.

*Depth*.—Approximately 3.8 cm.

*Fragrance*.—No fragrance.

*Lastingness*.—3 weeks, on average.

*Persistent*.—Self-cleaning.

*Petals*.—Quantity of Petals — 3 unfused petals; two conventional petals and one labellum. Arrangement — One lateral petal on each side. Length — Approximately 5.1 cm. Width — Approximately 5.2 cm. Shape — Near orbicular. Apex — Retuse to obtuse. Base — Cuneate. Margin — Entire; moderately undulate. Pubescence, texture and luster of upper surface — Glabrous, velvety and matte. Pubescence, texture and luster of lower surface — Glabrous, velvety and matte. Color when opening, upper surface — White, near RHS NN155A to NN155B, and margined purple, RHS N57B to N57D; petals are moderately dotted red-purple RHS 71A. Color when opening, lower surface — White, near RHS NN155A to NN155B, and margined purple, RHS N57B; petals are slightly dotted purple RHS N75B. Color when fully opened, upper surface — Purple, near RHS 76C to 76D, and margined purple, near N78A to N78D; petals are heavily dotted and blotched red-purple and purple, near RHS 71A, N78A and N78B, NN78A and NN78B. Color when fully opened, lower surface — Purple, near RHS 76A to 76B, and margined darker, near RHS 77B. Fading, upper surface — Not fading. Fading, lower surface — Not fading. Venation — Reticulate. Venation color, fully opened, upper surface — Purple, near RHS 76C to 76D, and margined purple, near RHS N78A to N78D. Venation color, fully opened, lower surface — Purple, near RHS 76A to 76B, and margined darker, near RHS 77B.

*Labellum*.—Shape — Three-lobed, lateral lobes involute, central lobe strongly revolute. Length — Central lobe — Approximately 2.2 cm. Lateral lobes — Approximately 1.3 cm. Width — Central lobe — Approximately 1.5 cm. Lateral lobes — Approximately 0.8 cm. Apex, central lobe — Emarginate. Apex, lateral lobes — Obtuse. Base, central and lateral lobes — Cuneate. Margin, central lobe — Entire; very slightly undulate. Margin, lateral lobes — Entire; not undulate. Texture and luster of upper surface — Central lobe — Glabrous, velvety, and matte; glossy at the apex. Lateral lobes — Glabrous, velvety, and matte; glossy at the apex. Texture and luster of lower surface — Central lobe — Glabrous, velvety, and matte; glossy at the apex. Lateral lobes — Glabrous, velvety, and matte. Color when opening, upper surface — Central lobe — Purple, near RHS NN78A. Lateral lobes — White, near RHS NN155A, and striped violet at the base, near RHS 83A; yellow dot present at the base, near RHS 14A. Color when opening, lower surface — Central lobe — Purple, near NN78A, and fading to white towards the base, near NN155A. Lateral lobes — White, near RHS NN155B, and slightly tinged purple, near RHS 76A to 76B. Color when fully opened, upper surface — Central lobe — Purple, near RHS N79C. Lateral lobes — Purple, near RHS N78B; yellow dot present at the base, near 13A to 13B. Color when fully opened, lower surface — Central lobe — Purple, near RHS N78A yet darker, and fading lighter towards the base, near 77C to 77D. Lateral lobes — Purple-violet, near N80C to N80D. Fading, upper surface — Not fading. Fading, lower surface — Not fading. Venation — Reticulate. Venation color, fully opened, upper surface — Central lobe — Purple, near RHS N79C. Lateral lobes — Purple, near RHS N78B; yellow dot present at the base, near 13A to 13B. Venation color, fully opened, lower surface — Central lobe — Purple, near RHS N78A yet darker, and fading lighter towards the base, near 77C to 77D. Lateral lobes — Purple-violet, near N80C to N80D.

*Callosities*.—Dimensions — 1.6 cm long and 0.7 cm wide, on average. Color — Purple, near RHS N78A.

*Spurs*.—Quantity — Average of 1. Length — Approximately 1.0 cm. Diameter — Approximately 0.6 cm. Vertical height — Approximately 0.9 cm, at the base. Shape — Short triangular. Apex — Bluntly acute. Base — Broad Cuneate. Pubescence, texture and luster — Glabrous, smooth, and matte. Color — Purple, near RHS 76A to 76B; apex is darker, near N75A.

*Sepals*.—Quantity — Average of 3 unfused sepals. Arrangement — One dorsal sepal and two lateral sepals. Length — Dorsal sepal — Approximately 5.5 cm. Lateral sepals — Approximately 6.3 cm. Width — Dorsal sepal — Approximately 5.6 cm. Lateral sepals — Approximately 6.8 cm. Shape, dorsal and lateral sepals — Broad ovate. Apex, dorsal and lateral sepals — Obtuse. Base, dorsal and lateral sepals — Cuneate. Margin, dorsal and lateral sepals — Entire; dorsal sepals are slightly undulate and lateral sepals are moderately undulate. Pubescence, texture and luster — Glabrous, velvety, and matte on both the upper and lower sepal surfaces. Color when opening, upper surface — Dorsal sepal — White, near RHS NN155A to NN155B, and margined purple, RHS N75B to N75D; sepals are moderately to heavily dotted red-purple RHS 71A. Lateral sepals — Same colorations as the dorsal sepal. Color when opening, lower surface — Dorsal sepal — White, near RHS NN155A to NN155B, and margined purple, RHS N75A; sepals are slightly dotted purple, RHS N75A to N75B. Lateral sepals — White, near RHS NN155A to NN155B, and tinged red-purple, near RHS 70A to 70C; margined purple RHS N75A; sepals are slightly dotted purple, RHS N75A to N75B. Color when fully opened, upper surface — Dorsal sepal — White, near RHS NN155A, and margined purple, RHS N78A to N78D; heavily dotted and blotched red-purple and purple, near RHS 71A, N78A and N78B, NN78A and NN78B. Lateral sepals — White, near RHS NN155A, and margined purple-violet, near RHS N80A; heavily dotted and blotched red-purple and purple, near RHS 71A, N78A and N78B. Color when fully opened, lower surface — Dorsal sepal — Purple, near RHS 76A to 76B, and margined darker, near RHS 77B. Lateral sepals — Purple, near RHS 76A to 76B, and margined darker, near RHS 77B. Fading, upper surface — The color of all sepals does not fade. Fading, lower surface — The color of all sepals does not fade. Venation — Reticulate. Venation color, fully opened, upper surface — Dorsal sepal — White, near RHS NN155A, and margined purple, RHS N78A to N78D; heavily dotted and blotched red-purple and purple, near RHS 71A, N78A and N78B, NN78A and NN78B. Lateral sepals — White, near RHS NN155A, and margined purple-violet, near RHS N80A; heavily dotted and blotched red-purple and purple, near RHS 71A, N78A and N78B. Venation color, fully opened, lower surface — Dorsal sepal — Purple, near RHS 76A to 76B, and margined darker, near RHS 77B. Lateral sepals — Purple, near RHS 76A to 76B, and margined darker, near RHS 77B.

*Pedicels*.—Length — Approximately 7.4 cm. Diameter — Approximately 0.6 cm. Angle — Approximately 70 degree angle to peduncle axis. Strength — Moderate. Texture — Glabrous, axially angled with 5 "ribs", axially twisted (due to resupination). Luster — Glossy. Color — White RHS N155A; tinged purple towards the distal end, near RHS 76A to 76B, and yellow-green towards the proximal end, near RHS 147C to 147D.

*Bract*.—Quantity — One bract present at the base of each pedicel. Shape — Reniform; folded around the base of each pedicel. Dimensions — Average of 1.1 cm long and 1.6 cm wide. Apex — Broad acute. Base — Broad Cuneate. Margins — Entire. Color, both surfaces — Yellow-green, in between RHS N144C and N144D.

Reproductive organs:

*Column*.—Length — Approximately 0.7 cm. Diameter — Approximately 0.8 cm. Color — Green-white RHS 157D.

*Ovary*.—Position — Inferior. Diameter — Approximately 1.2 cm. Color — Yellow-green RHS 150B.

*Pollinia color*.—Yellow-orange RHS 21B.

Seed and fruit: No fruit and seed production has been detected to date.

COMPARISON WITH THE PARENT AND MOST SIMILAR *VANDA* CULTIVAR KNOWN TO THE INVENTOR

Plants of the new cultivar 'SPCDW1504' are most similar to the parent, *Vanda* 'SPCDW0801' (unpatented in the United States, Community Plant Variety Rights grant number 28272). The parent is also the closest known commercial comparator. A comparison of 'SPCDW1504' with *Vanda* 'SPCDW0801' is described in Chart 1.

CHART 1

| Characteristic | 'SPCDW1504' | 'SPCDW0801' |
|---|---|---|
| Average foliage dimensions. | 25.4 cm long and 3.1 cm wide. | 26.6 cm long and 3.3 cm wide. |
| Average flower dimensions | Vertical height is 11.3 cm; diameter is 10.5 cm. | Vertical height is 12.8 cm; diameter is 11.3 cm. |
| General coloration of petals when opening, upper surface | White; margined purple; moderately to heavily dotted red-purple. | White; margined violet, moderately to heavily dotted purple to violet. |
| General coloration of petals when opening, lower surface | White; margined purple; slightly dotted purple. | White; margined violet; slightly dotted violet. |
| General coloration of petals when fully open, upper surface | Purple; margined purple; heavily dotted and blotched red-purple and purple. | Purple; margins violet with outer edge lighter; base violet; heavily dotted and blotched purple, purple-violet and violet. |
| General coloration of petals when fully open, lower surface | Purple; margined darker purple. | Violet; margined darker violet; slightly dotted violet. |
| Petal venation when fully opened, upper surface | Purple; margined darker purple. | Purple; margins violet with outer edge lighter; base violet; heavily dotted and blotched purple, purple-violet and violet. |
| Petal venation when fully opened, upper surface | Purple; margined darker purple; darker than upper surface | Violet; margined darker violet; slightly dotted violet. |
| Labellum, central lobe coloration when fully open, upper surface | Purple. | Violet-blue and fading violet towards the base. |
| Labellum, central lobe coloration when fully open, lower surface | Purple and fading to lighter purple towards the base. | Violet and fading lighter towards the base; apex is violet-blue. |
| Average sepal length | Dorsal sepal is 5.5 cm long; lateral sepals are 6.3 cm long. | Dorsal sepal is 5.8 cm long; lateral sepals are 6.3 cm long. |
| General coloration of sepals when opening, upper surface | Dorsal sepal and lateral sepals are white and margined purple; moderately to heavily dotted red-purple. | Lateral sepals and dorsal sepal white; margined violet; margins on lateral sepals slightly more bluish; moderately to heavily dotted purple to violet. |
| General coloration of sepals when opening, lower surface | Dorsal sepal and lateral sepals white margined purple; slightly dotted purple; lateral sepals tinged red-purple. | Lateral sepals and dorsal sepal green-white; margined violet; slightly dotted violet. |
| General color ation of sepals when fully open, upper surface | Dorsal sepal white; margined purple; heavily dotted and blotched red-purple and purple. Lateral sepals white; margined purple-violet; heavily dotted and blotched red-purple and purple. | Dorsal sepal and lateral sepals purple; margins darker purple; outer edge lighter purple; heavily dotted and blotched purple, purple-violet and violet. |
| General coloration of sepals when fully open, lower surface | Purple; margined darker purple. | Dorsal sepal and lateral sepals violet; margined purple; slightly dotted violet. |

CHART 1-continued

| Characteristic | 'SPCDW1504' | 'SPCDW0801' |
|---|---|---|
| Sepal venation color when fully open, upper sepal surface | Dorsal sepal white; margined purple; heavily dotted and blotched red-purple and purple. Lateral sepals white; margined purple-violet; heavily dotted and blotched red-purple and purple. | Dorsal sepal and lateral sepals purple; margins are darker purple; near outer edge lighter purple; heavily dotted and blotched purple, purple-violet and violet. |

CHART 1-continued

| Characteristic | 'SPCDW1504' | 'SPCDW0801' |
|---|---|---|
| Sepal venation color when fully open, lower sepal surface | Purple; margined darker purple. | Dorsal sepal and lateral sepals violet; margined darker violet; slightly dotted violet. |

That which is claimed is:

1. A new and distinct variety of *Vanda* plant named 'SPCDW1504', substantially as described and illustrated herein.

* * * * *